United States Patent [19]
Nakazato et al.

[11] Patent Number: 5,990,151
[45] Date of Patent: Nov. 23, 1999

[54] OPTICALLY ACTIVE SUBSTITUTED PHENYLALKYLAMINE DERIVATIVES

[75] Inventors: Atsuro Nakazato; Toshihito Kumagai; Tomoki Miyazawa; Koumei Ohta; Yutaka Kawashima, all of Tokyo, Japan; Katsuo Hatayama, deceased, late of Tokyo, Japan, by Sachiko Hatayama, legal representative

[73] Assignee: Taisho Pharmaceutical Co., Ltd., Japan

[21] Appl. No.: 08/981,539

[22] PCT Filed: Jun. 13, 1996

[86] PCT No.: PCT/JP96/01613

§ 371 Date: May 15, 1998

§ 102(e) Date: May 15, 1998

[87] PCT Pub. No.: WO97/00238

PCT Pub. Date: Jan. 3, 1997

[30] Foreign Application Priority Data

Jun. 14, 1995 [JP] Japan .................. 7-147180

[51] Int. Cl.[6] .................. A61K 31/135; A61K 31/38; C07D 333/06
[52] U.S. Cl. .................. 514/438; 514/641; 514/649; 514/650; 549/75; 564/271; 564/272; 564/276; 564/355; 564/360
[58] Field of Search .................. 514/438, 641, 514/649, 650; 549/75; 564/271, 272, 276, 355, 360

[56] References Cited

U.S. PATENT DOCUMENTS 4,329,367 5/1982 Francis .................. 424/330
4,971,995 11/1990 Schoofs et al. .................. 514/520

FOREIGN PATENT DOCUMENTS

0418430A1 9/1989 European Pat. Off. .
0641766A1 9/1992 European Pat. Off. .
2626877 11/1989 France .
9011997 10/1990 WIPO .

Primary Examiner—Johann Richter
Assistant Examiner—John F. Dolan
Attorney, Agent, or Firm—Lorusso & Loud

[57] ABSTRACT

The present invention relates to an optically active, substituted phenylalkylamine derivative represented by Formula [1]:

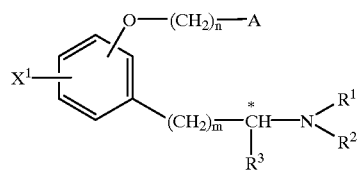

wherein A is a substituted or non-substituted phenyl or thienyl; $X^1$ is hydrogen, halogen, hydroxyl or a substituted or non-substituted $C_{1-5}$ alkoxy; $R^1$ and $R^2$ are equally or differently hydrogen, $C_{1-7}$ alkyl, $C_{3-7}$ alkenyl or $C_{3-7}$ alkynyl; $R^3$ is $C_{1-10}$ alkyl, $C_{2-10}$ alkenyl or $C_{2-10}$ alkynyl; n is an integer from 2 to 5; and m is an integer from 1 to 4, or a pharmaceutically acceptable salt thereof, and pharmaceutical use of such compound or salt. The compound of the invention is excellent in sigma 1 receptor antagonism and useful for treating schizophrenia, depression, anxiety, cerebrovascular diseases/senile troublesome behaviors, and cognitive dysfunctions and motor dysfunctions such as Alzheimer's disease, Parkinson's disease and Huntington's disease which are neurodegenerative diseases. Further, the compound of the invention is also useful for treating dependence resulted from drug abuse.

6 Claims, No Drawings

OPTICALLY ACTIVE SUBSTITUTED PHENYLALKYLAMINE DERIVATIVES

This application is a 371 of PCT/JP96/01613 filed on Jun. 13, 1996.

1. Technical Field

The present invention relates to optically active, substituted phenylalkylamine derivatives having an antipsychotic action.

2. Background Art

Antipsychotic agents are used for treating not only schizophrenia but also troublesome behaviors in cerebrovascular diseases and senile dementia (aggressive behaviors, mental excitement, poriomania, delirium, etc.).

However, conventional antipsychotic agents cause strong extrapyramidal disorders and thus their use has become a serious problem. In order to solve this problem, recent development of antipsychotic agents has been made by an approach utilizing a mode of action of drugs which is quite different from that of conventional drugs.

One of the thus developed antipsychotic agents is a sigma receptor antagonist. Sigma receptors are classified into sigma 1 receptor and sigma 2 receptor (Trends in Pharmacological Sciences, Vol. 13, pp. 85–86). It has been made clear that pentazocine (Clinical Pharmacology and Therapeutics, Vol. 9, pp. 142–151) and SKF10047 (N-arylnormethazocine) (Advances in Chemistry Series, Vol. 45, pp. 170–176) which develop psychotic symptoms in humans have high affinity for sigma 1 receptor (agonist) (Trends in Pharmacological Sciences, Vol. 13, pp. 85–86). A sigma receptor, particularly, sigma 1 receptor is considered to be a receptor involved in mental aberration such as hallucination symptoms. Compounds having specific affinity for this receptor exhibit an antipsychotic action without causing extrapyramidal disorders.

As a sigma antagonist, Rimcazole is known, for example. However, both its specificity to and affinity for sigma 1 receptor are not sufficient.

DISCLOSURE OF THE INVENTION

It is an object of the present invention to provide novel compounds which have an antipsychotic action without causing extrapyramidal disorders.

As a result of extensive and intensive researches on optically active, substituted phenylalkylamine derivatives, the present inventors have found novel optically active, substituted phenylalkylamine derivatives which have specific and high affinity for sigma 1 receptor. Thus, the present invention has been achieved.

Hereinbelow, the present invention will be described.

The present invention includes the following inventions.

(1) An optically active, substituted phenylalkylamine derivative represented by Formula [1]:

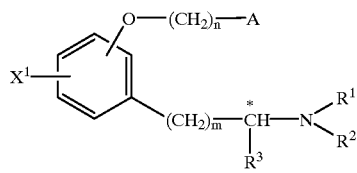

wherein A is a substituted or non-substituted phenyl or thienyl; $X^1$ is hydrogen, halogen, hydroxyl or a substituted or non-substituted $C_{1-5}$ alkoxy; $R^1$ and $R^2$ are equally or differently hydrogen, $C_{1-7}$ alkyl, $C_{3-7}$ alkenyl or $C_{3-7}$ alkynyl; $R^3$ is $C_{1-10}$ alkyl, $C_{2-10}$ alkenyl or $C_{2-10}$ alkynyl; n is an integer from 2 to 5; and m is an integer from 1 to 4, or a pharmaceutically acceptable salt thereof.

(2) The compound of (1), wherein $R^3$ is $C_4$ or $C_5$ alkyl in Formula [1].

(3) The compound of (1), wherein $R^1$ is 3-methylbutyl in Formula [1].

(4) The compound of (1), wherein $R^1$ is hydrogen; $R^2$ is propyl; $R^3$ is 3-methylbutyl or butyl; $X^1$ is 4-methoxy; and A-$(CH_2)$n-O is 3-(2-phenylethoxy) in Formula [1].

(5) Use of the compound of (1) as an antipsychotic agent.

(6) Use of the compound of (1) as a sigma 1 receptor antagonist.

(7) A method for blocking sigma 1 receptor, comprising using the compound of (1).

In the present invention, as the substituted phenyl represented by A, phenyl which is substituted by any one to three substituents selected from halogen, hydroxyl and $C_{1-5}$ alkoxy may be used.

In the present invention, the term "halogen" means fluorine, chlorine, bromine or iodine.

The $C_{1-5}$ alkoxy is a straight-chain or branched-chain alkoxy such as methoxy, ethoxy, propoxy, isopropoxy, butoxy, isobutoxy, t-butoxy, pentoxy, 3-methylbutoxy, etc. These alkoxys may be substituted by, for example, phenyl. As $C_{1-5}$ alkoxy substituted by phenyl, benzyloxy, 2-phenylethoxy, 3-phenylpropoxy and the like may be enumerated.

The $C_{1-7}$ alkyl represented by $R^1$ or $R^2$ is straight-chain, branched-chain or cyclic alkyl, or alkyl substituted by cyclic alkyl. Specific examples include methyl, ethyl, propyl, isopropyl, cyclopropyl, butyl, isobutyl, cyclopropylmethyl, pentyl, isoamyl, 3-methylbutyl, cyclobutylmethyl, hexyl, 4-methylpentyl, 2-ethylbutyl, cyclopentylmethyl, heptyl, 5-methylhexyl and cyclohexylmethyl. Preferable are propyl, isopropyl, cyclopropyl, butyl and the like.

The $C_{3-7}$ alkenyl represented by $R^1$ or $R^2$ is straight-chain or branched-chain alkenyl such as 2-propenyl, 3-methyl-2-butenyl, etc.

The $C_{3-7}$ alkynyl represented by $R^1$ or $R^2$ is straight-chain or branched-chain alkynyl such as 2-propynyl, 4-methyl-2-pentynyl, etc.

The $C_{1-10}$ alkyl represented by $R^3$ is straight-chain, branched-chain or cyclic alkyl or alkyl substituted by cyclic alkyl. Specific examples include methyl, ethyl, propyl, isopropyl, butyl, isobutyl, 2-butyl, cyclopropylmethyl, pentyl, isoamyl, 2-pentyl, 3-pentyl, 3-methylbutyl, cyclobutylmethyl, hexyl, 4-methylpentyl, 2-hexyl, 3-hexyl, 2-ethylbutyl, cyclopentylmethyl, heptyl, 3-ethylpentyl, cyclohexylmethyl, octyl, 6-methylheptyl, 2-octyl, 3-octyl, 4-octyl, 2-propylpentyl, 2-cyclohexylethyl, nonyl, 7-methyloctyl, 2-nonyl, 3-nonyl, 4-nonyl, 5-nonyl, 3-propylhexyl, decyl, 8-methylnonyl, 2-decyl, 3-decyl, 4-decyl, 5-decyl and 2-butylhexyl. Preferable are butyl, pentyl, isoamyl, 2-pentyl, 3-pentyl and 3-methylbutyl.

The $C_{2-10}$ alkenyl represented by $R^3$ is straight-chain or branched-chain alkenyl such as vinyl, 2-propen-1-yl, 3-buten-1-yl, 3-methyl-2-buten-1-yl, etc. Preferable is 3-methyl-2-buten-1-yl.

The $C_{2-10}$ alkynyl represented by $R^3$ is straight-chain or branched-chain alkenyl such as ethynyl, 2-propynyl, 4-methyl-2-pentynyl, etc.

As the pharmaceutically acceptable salt of the compound of the invention, for example, a salt formed by the compound and a mineral acid such as sulfuric acid, hydrochloric acid, phosphoric acid, etc.; and a salt formed by the compound and an organic acid such as acetic acid, oxalic acid, lactic acid, tartaric acid, fumaric acid, maleic acid, trifluoroacetic acid, methanesulfonic acid, etc. may be enumerated.

The compound of the invention represented by Formula [1] can be prepared by the procedures described below.

In the following reaction formulas, $R^4$ and $R^5$ are equally or differently $C_{1-6}$ alkyl or benzyl; $R^6$ is $C_{1-10}$ alkyl; $R^7$ is $C_{1-6}$ alkyl or benzyl; $R^8$ is $C_{1-7}$ alkyl, $C_{3-7}$ alkenyl or $C_{3-7}$ alkynyl; X is any halogen; $R^1$, $R^2$, $R^3$, $X^1$, A, m and n are as defined previously.

ethyl acetate; alcohols such as methanol, ethanol; ethers such as tetrahydrofuran, 1,2-dimethoxyethane; hydrocarbons such as toluene and benzene; and organic carboxylic acids such as acetic acid.

Step C: Hydrolysis of carboxylic acid ester [8] is performed in a solvent, for example alcohols such as methanol and ethanol, ethers such as tetrahydrofuran and dioxane, ketones such as acetone, 2-butanone, or a mixed solvent composed of one of these substances and water in the presence of a base at 0–150° C., preferably 0–90° C., to thereby obtain carboxylic acid [2]. Specific examples of the

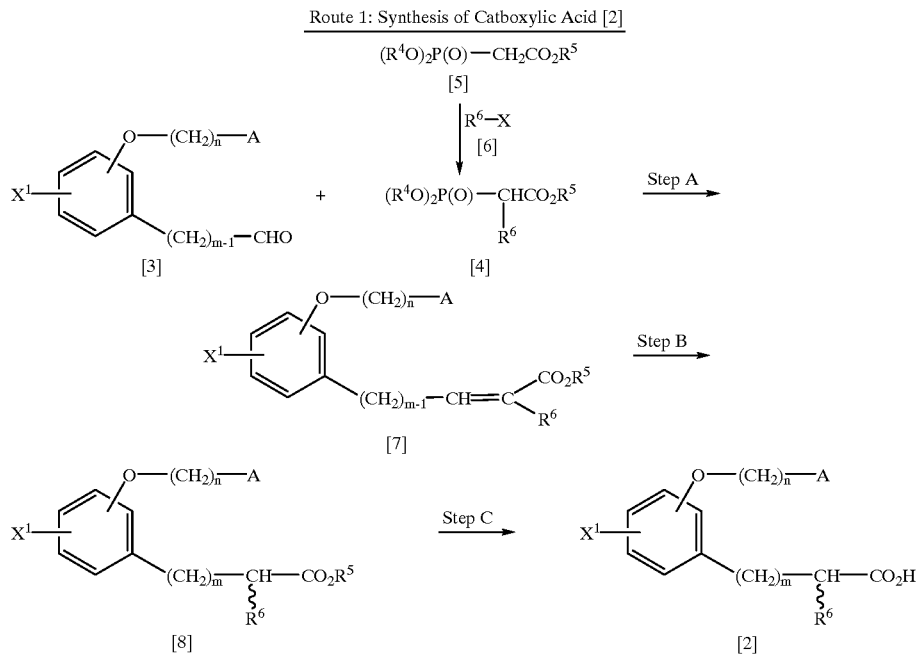

Carboxylic acid [2] is obtained by subjecting aldehyde [3] and phosphonoacetic acid derivative [41] generated from compound [5] by the method described in a reference (J. Am. Chem. Soc., Vol. 83, p. 1773, (1961)) to Wittig-Horner reaction, reducing the resultant double bond and then hydrolyzing the resultant product.

Step A: Wittig-Horner reaction of aldehyde [3] with phosphonoacetic acid derivative [4] generated from compound [5] and alkyl halide [6] by the method described in the above reference is performed in a solvent inactive in the reaction, in the presence of a base, at −78 to 150° C., preferably at 0–100° C. to thereby obtain unsaturated carboxylic acid ester [7]. Specific examples of the above solvent inactive in the reaction include alcohols such as methanol, ethanol, isopropanol; ethers such as diethyl ether, tetrahydrofuran, 1,2-dimethoxyethane; hydrocarbons such as toluene and benzene; or water. Specific examples of the above base include sodium methoxide, sodium ethoxide, potassium t-butoxide, potassium carbonate, sodium carbonate, sodium hydride and potassium bis(trimethylsilyl) amide.

Step B: Reduction of the double bond of unsaturated carboxylic acid ester [7] is performed, for example, by hydrogenating the ester in a solvent with a metal catalyst such as palladium carbon, platinum dioxide, Raney nickel or the like to obtain carboxylic acid ester [8]. Specific examples of the above solvent include carboxylic acid esters such as above base include sodium hydroxide, potassium hydroxide, lithium hydroxide and potassium carbonate.

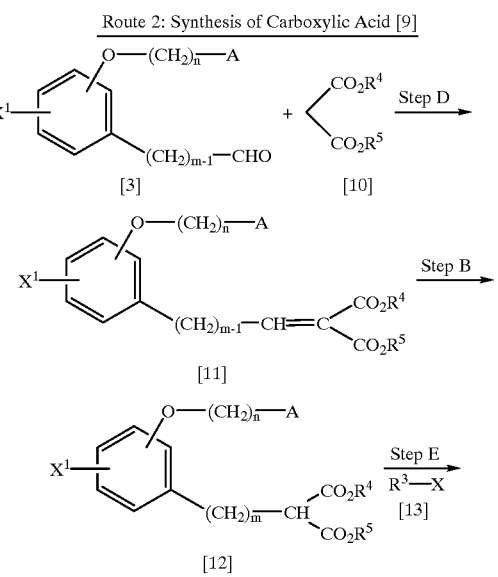

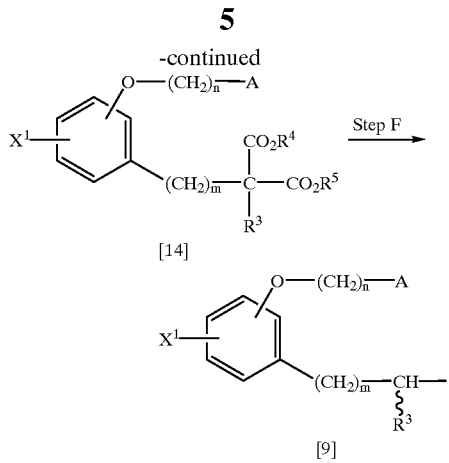

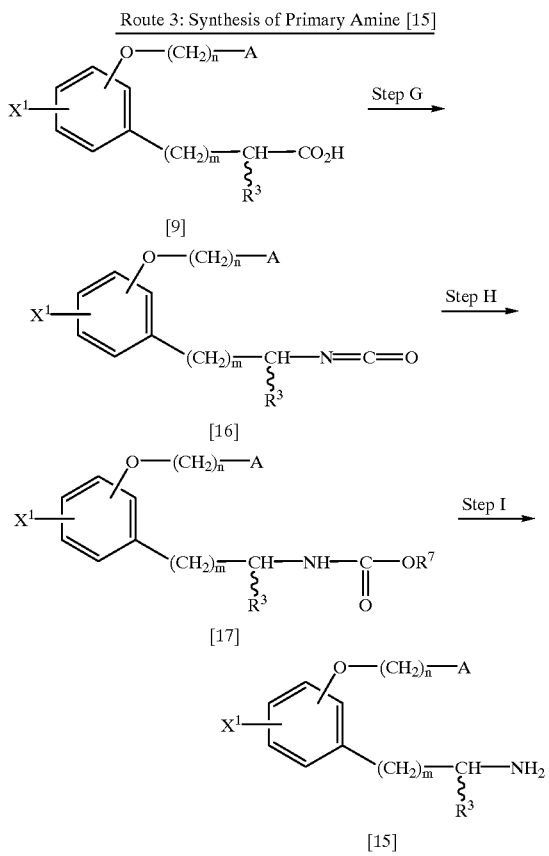

Route 3: Synthesis of Primary Amine [15]

Carboxylic acid [9] is obtained by condensing aldehyde [3] and malonic acid diester [10], reducing the resultant double bond, alkylating (or alkenylating or alkynylating) the product, and then hydrolyzing and decarboxylating the resultant product.

Step D: Condensation of aldehyde [3] and malonic acid diester [10] is performed in an organic solvent in the presence of an amine or a salt thereof to generate unsaturated dicarboxylic acid ester [11]. Specific examples of the above organic solvent include alcohols such as methanol, ethanol, isopropanol; ethers such as diethyl ether, tetrahydrofuran, 1,2-dimethoxyethane; and hydrocarbons such as toluene and benzene. Specific examples of the above amine or salt thereof include amines such as ammonia, diethylamine, pyrrolidine, piperidine, piperazine, morpholine, or salts formed by such amines and hydrochloric acid, acetic acid, benzoic acid, etc.

Subsequently, unsaturated dicarboxylic acid ester [11] is hydrogenated in the same manner as in Step B, to thereby obtain dicarboxylic acid ester [12].

Step E: Dicarboxylic acid ester [12] is reacted with halide [13] in an organic solvent in the presence of a base to thereby obtain substituted dicarboxylic acid ester [14]. Specific examples of the above organic solvent include alcohols such as methanol, ethanol, isopropanol; ethers such as diethyl ether, tetrahydrofuran, 1,2-dimethoxyethane; and hydrocarbons such as toluene and benzene. Specific examples of the above base include sodium methoxide, sodium ethoxide, potassium t-butoxide, potassium carbonate, sodium carbonate, sodium hydride and potassium bis(trimethylsilyl) amide.

Step F: Hydrolysis of substituted dicarboxylic acid ester [14] is performed in a solvent inactive in the reaction in the presence of a base at room temperature to 250° C., preferably at 50–150° C., to generate a metal salt of the substituted dicarboxylic acid. Specific examples of the above solvent inactive in the reaction include alcohols such as methanol, ethanol, ethylene glycol; ethers such as dioxane; ketones such as acetone, 2-butanone; water or a mixture thereof. Specific examples of the above base include sodium hydroxide, potassium hydroxide, lithium hydroxide and potassium carbonate.

Subsequently, the thus obtained metal salt is treated with an acid to thereby produce a substituted dicarboxylic acid, which is heated to 50–250° C., preferably 70–170° C., in a solvent inactive in the reaction or without any solvent for decarboxylation. Thus, carboxylic acid [9] is obtained. Specific examples of the above acid include inorganic acids such as hydrochloric acid and sulfuric acid. Specific examples of the above solvent inactive in the reaction include hydrocarbons such as benzene, toluene, xylene, ethers such as dioxane, alcohols such as isopropanol, and water.

Carboxylic acid [9] is led to a primary amine represented by formula [15] through Curtius Rearrangement (see, for example, J. Am. Chem. Soc., Vol. 94, p. 6203 (1972); J. Praktische Chemie, Vol. 50, p. 275 (1894)) usually employed.

Step G: Carboxylic acid [9] is heated to 40–150° C. in the presence of diphenylphosphoryl azide and a base in a solvent inactive in the reaction to thereby obtain isocyanate [16] through acyl azide. Specific examples of the above base include triethylamine, diisopropylethylamine and pyridine, and specific examples of the above solvent inactive in the reaction include benzene, toluene, tetrahydrofuran and dioxane.

Alternatively, isocyanate [16] can also be obtained by converting carboxylic acid [9] into a mixed acid anhydride, acid halide or the like and then reacting it with sodium azide or potassium azide according to conventional methods (see, for example, Organic Syntheses, Col.Vol.III, p. 846 (1955)).

Step H: Isocyanate [16] is heated with an alcohol to generate carbamic acid ester [17]. Specific examples of the above alcohol include methanol, ethanol, propanol, isopropanol, butanol, isobutanol, t-butanol and benzyl alcohol.

When the alcohol described above is used in Step G as a reaction solvent, the reaction generates a corresponding carbamic acid ester [17] through an acyl azide and isocyanate [16].

Step I: Carbamic acid ester [17] is led to a primary amine represented by formula [15] through hydrolysis with a base or acid in a solvent. Specific examples of the above solvent include methanol, ethanol, isopropyl ether, dioxane, ethyl acetate, dichloromethane, benzene, toluene, water or a mixed solvent composed of an organic solvent and water. Specific examples of the above base include sodium hydroxide, potassium hydroxide and barium hydroxide, and specific examples of the above acid include hydrochloric acid, hydrogen chloride, hydrogen bromide, sulfuric acid, acetic acid and trifluoroacetic acid.

Further, a benzyl ester of carbamic acid which is obtained if benzyl alcohol is used in Step H generates a primary amine represented by formula [15], for example, by hydrogenating the ester in a solvent with a metal catalyst such as palladium carbon, palladium hydroxide on carbon, Raney nickel or the like. Specific examples of the above solvent include carboxylic esters such as ethyl acetate; alcohols such as methanol, ethanol; ethers such as tetrahydrofuran, 1,2-dimethoxyethane; hydrocarbons such as toluene, benzene; and organic carboxylic acids such as acetic acid.

Route 4: Optical Resolution of the Primary Amine

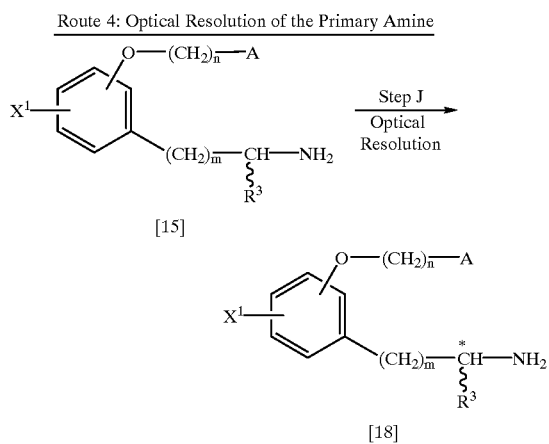

Step J: When converted into a salt of an optically active carboxylic acid, sulfonic acid or the like and then recrystallized in a solvent, primary amine [15] generates optically active primary amine [18] which is the compound of the invention. The optically active carboxylic acid or sulfonic acid mentioned above is an optically active organic carboxylic acid such as (−)- or (+)-mandelic acid, (−)- or (+)-O,O'-dibenzoyltartaric acid, (−)- or (+)-camphoric acid, abietic acid, (−)- or (+)-camphor-10-sulfonic acid, (−)- or (+)-tartaric acid, etc. or an N-protected amino acid of L- or D-form. Specific examples of the above solvent include alcohols such as ethanol, isopropanol; hydrocarbons such as benzene, toluene; organic carboxylic acid esters such as ethyl acetate; haloalkyls such as dichloromethane; and water. These solvents may be used independently or in combination.

Route 5: Synthesis of Secondary Amine [19] and Tertiary Amine [20]

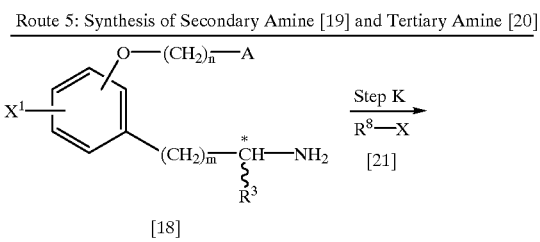

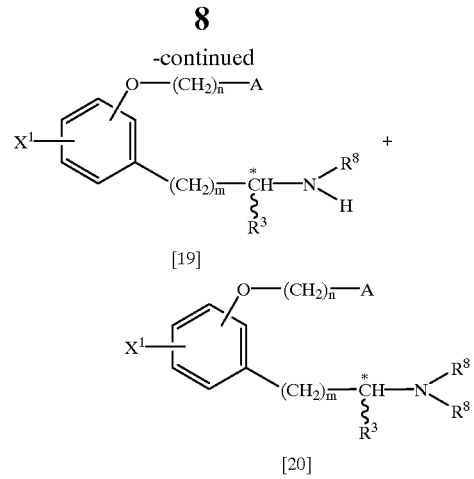

Step K: Optically active primary amine [18] is reacted with halide [21] in the presence of a base in a solvent inactive in the reaction at 0–150° C., preferably at room temperature to 90° C., for 8 hours to 4 days to thereby produce secondary amine [19] and tertiary amine [20] which are the compounds of the invention. When one equivalent of halide [21] is used in the above reaction, secondary amine [19] is produced preferentially. When 1.5 equivalents of halide [20] is used, secondary amine [19] and tertiary amine [20] are produced. When 2 equivalents or more of halide [21] is used, tertiary amine [20] is produced preferentially. The base mentioned above is, for example, an inorganic base such as potassium carbonate, sodium carbonate, sodium hydrogencarbonate, sodium hydroxide, etc.; or an organic base such as triethylamine, diisopropylethylamine, pyridine, etc. The solvent inactive in the reaction mentioned above is, for example, N,N-dimethylformamide, acetonitrile, methanol, ethanol, toluene, tetrahydrofuran, water or the like.

The compound of the invention is excellent in sigma 1 receptor antagonism and useful for treating schizophrenia, depression, anxiety, cerebrovascular diseases/senile troublesome behaviors, and cognitive dysfunctions and motor dysfunctions such as Alzheimer's disease, Parkinson's disease and Huntington's disease which are neurodegenerative diseases. Further, the compound of the invention is also useful for treating dependence resulted from drug abuse (narcotics, antihypnotics, alcohols, psychotropics, marihauna, etc.).

For the purposes described above, the compound of the invention may be combined with a conventional excipient, binder, disintegrator, pH modifier, solubilizer, etc. and formulated into tablets, pills, capsules, granules, powder, liquid preparation, an emulsion, a suspension, an injection, etc. in usual pharmaceutical techniques.

The compound of the invention may be administered to adult patients orally or parenterally once or several times a day at a dose of 0.1–500 mg/day. This dose may be appropriately adjusted depending on the kind of the disease to be treated and the age, weight and symptoms of the patient.

BEST MODE FOR CARRYING OUT THE INVENTION

The present invention will be described more specifically below with the following Examples and Test Examples.

EXAMPLE 1

Synthesis of N-t-Butoxycarbonyl-1-Pentyl-2-[4-Methoxy-3-(2-Phenylethoxy)phenyl]ethylamine (1) To a suspension of 60% sodium hydride (oily)(0.847 mg) in 25 ml of 1,2-dimethoxyethane, 4.20 ml of triethyl phosphonoacetate was added dropwise over 10 minutes and stirred at room temperature for 1 hour. To this reaction solution, 2.65 ml of pentyl bromide was added, and then refluxed by heating for 3 hours under stirring. Thereafter, the reaction solution was cooled to room temperature and 0.857 mg of 60% sodium hydride (oily) was added thereto. After stirring at room temperature for 30 minutes, 5.15 g of 4-methoxy-3-(2-phenylethoxy)-benzaldehyde was added and refluxed by heating for 2 hours under stirring. Then, the reaction solution was cooled to room temperature, and ethyl acetate and water was added thereto to separate the solution into layers. The organic layer separated was washed with water, an aqueous solution of saturated sodium hydrogencarbonate and a saturated aqueous solution of NaCl in consecutive order and dried over anhydrous magnesium sulfate. The drying agent was separated by filtration, and then the filtrate was concentrated under reduced pressure. The residue was purified by silica gel column chromatography (hexane/ethyl acetate=30:1) to thereby obtain 5.39 g of ethyl 3-[4-methoxy-3-(2-phenylethoxy)phenyl]-2-pentylacrylate as a mixture of E- and Z-isomers (E-isomer:Z-isomer=7.0:1).

(2) The above isomer mixture (5.16 g) was dissolved in 25 ml of ethanol, and 0.52 g of 5% Pd/C was added to hydrogenate at room temperature. After the completion of the reaction, 5% Pd/C was separated through a Celite plate and the filtrate was concentrated under reduced pressure to thereby obtain crude ethyl 3-[4-methoxy-3-(2-phenylethoxy)phenyl]-2-pentylpropionate. This crude compound was used in the subsequent step without purification.

(3) To the above residue, another 25 ml of ethanol and a solution of 3.65 g of potassium hydroxide in 3.7 ml of water were added and stirred overnight at room temperature. After concentration of the reaction solution under reduced pressure, the residue was dissolved in 50 ml of water. To this solution, concentrated hydrochloric acid was added dropwise to make it acidic. Then, the resultant solution was extracted with ethyl acetate. The ethyl acetate extract was washed with a saturated aqueous solution of NaCl and dried over anhydrous magnesium sulfate. The drying agent was separated by filtration, and then the filtrate was concentrated under reduced pressure to obtain 4.75 g of crude 3-[4-methoxy-3-(2-phenylethoxy)-phenyl]-2-pentylpropionic acid. This crude compound was used in the subsequent step without purification.

(4) To a solution of the crude 3-[4-methoxy-3-(2-phenylethoxy)-phenyl]-2-pentylpropionic acid (4.01 g) in 40 ml of benzene, 1.65 ml of triethylamine and 2.6 ml of diphenylphosphoryl azide were added and refluxed by heating for 2 hours. Then, the reaction solution was concentrated under reduced pressure. To the residue, 20 ml of t-butanol was added and refluxed by heating for 12 hours. Then, the reaction solution was concentrated under reduced pressure. The residue was dissolved in 50 ml of ethyl acetate, washed with an aqueous solution of 0.5 N sodium hydroxide, an aqueous solution of 5% potassium hydrogensulfate, a saturated aqueous solution of sodium hydrogencarbonate and a saturated aqueous solution of NaCl in consecutive order and dried over anhydrous magnesium sulfate, followed by concentration of the filtrate under reduced pressure. The residue was purified by silica gel column chromatography (hexane/ethyl acetate=25:1). Recrystallization from hexane yielded 3.08 g of N-t-butoxycarbonyl-1-pentyl-2-[4-methoxy-3-(2-phenylethoxy)-phenyl]ethylamine.

m.p. 91.5–92.5° C.

The following compounds were obtained in the same manner.

N-t-butoxycarbonyl-1-propyl-2-[4-methoxy-3-(2-phenylethoxy)-phenyl]ethylamine m.p. 89.3–90.3° C. (recrystallized from hexane)

N-t-butoxycarbonyl-1-butyl-2-[4-methoxy-3-(2-phenylethoxy)-phenyl]ethylamine m.p. 101.5–102.0° C. (recrystallized from hexane)

N-t-butoxycarbonyl-1-hexyl-2-[4-methoxy-3-(2-phenylethoxy)-phenyl]ethylamine m.p. 85.0–86.0° C. (recrystallized from hexane)

N-t-butoxycarbonyl-1-heptyl-2-[4-methoxy-3-(2-phenylethoxy)-phenyl]ethylamine m.p. 82.5–83.5° C. (recrystallized from hexane)

N-t-butoxycarbonyl-1-octyl-2-[4-methoxy-3-(2-phenylethoxy)-phenyl]ethylamine m.p. 80.5–80.8° C. (recrystallized from hexane)

N-t-butoxycarbonyl-1-(3-methylbutyl)-2-[4-methoxy-3-(2-phenylethoxy)phenyl]ethylamine m.p. 103.1–103.8° C. (recrystallized from hexane)

N-t-butoxycarbonyl-1-cyclopropylmethyl-2-[4-methoxy-3-(2-phenylethoxy)phenyl]ethylamine m.p. 88.8–89.5° C. (recrystallized from hexane)

N-t-butoxycarbonyl-1-(2-methylpropyl)-2-[4-methoxy-3-(2-phenylethoxy)phenyl]ethylamine m.p. 89.6–90.3° C. (recrystallized from ethyl acetate-hexane)

N-t-butoxycarbonyl-1-(4-methylpentyl)-2-[4-methoxy-3-(2-phenylethoxy)phenyl]ethylamine m.p. 87.7–88.3° C. (recrystallized from ethyl acetate-hexane)

EXAMPLE 2

Synthesis of N-t-Butoxycarbonyl-1-Ethyl-2-[4-Methoxy-3-(2-Phenylethoxy)phenyl]ethylamine (1) A mixture of 4-methoxy-3-(2-phenylethoxy) benzaldehyde (5.09 g), triethyl 2-phosphonobutyrate (10.76 g) and an aqueous solution of 6 M potassium carbonate (8.3 ml) was heated to 150° C. (oil bath temperature) and stirred vigorously for 8 hours. After the reaction mixture was cooled to room temperature, it was extracted with toluene. The toluene extract was washed with an aqueous solution of 0.5 N sodium hydroxide and a saturated aqueous solution of NaCl in consecutive order and dried over anhydrous magnesium sulfate. The drying agent was separated by filtration, and the filtrate was concentrated under reduced pressure. The residue was purified by silica gel column chromatography (hexane/ethyl acetate=25:1) to obtain 4.08 g of ethyl 3-[4-methoxy-3-(2-phenylethoxy)phenyl]-2-ethylacrylate as a mixture of E- and Z-isomers (E-isomer:Z-isomer=5. 7:1).

(2) The above isomer mixture (3.88 g) was treated in the same manner as described in (2) in Example 1 to obtain crude ethyl 3-[4-methoxy-3-(2-phenylethoxy)phenyl]-2-ethylpropionate. This crude compound was used in the subsequent step without purification.

(3) The above residue was treated in the same manner as described in (3) in Example 1 to obtain 3.50 g of crude 3-[4-methoxy-3-(2-phenylethoxy)phenyl]-2-ethylpropionic acid. This crude compound was used in the subsequent step without purification.

(4) The crude 3-[4-methoxy-3-(2-phenylethoxy)phenyl]-2-ethylpropionic acid (3.41 g) was treated in the same manner as described in (4) in Example 1. Recrystallyzation from hexane yielded 2.52 g of N-t-butoxycarbonyl-1-ethyl-2-[4-methoxy-3-(2-phenylethoxy)-phenyl]ethylamine.

m.p. 88.5–89.5° C.

The following compounds were obtained in the same manner.

N-t-butoxycarbonyl-1-methyl-2-[4-methoxy-3-(2-phenylethoxy)-phenyl]ethylamine

NMR (CDCl$_3$) δ(ppm); 1.05(3H,d, J=6.6 Hz),1.40(9H,s), 2.56(1H,dd,J=7.5,13.5 Hz), 2.75(1H,dd,J=5.8,13.5 Hz), 3.16(2H,t,J=7.6 Hz), 3.83(1H,m), 3.84(3H,s), 4.19(2H, t, J=7.6 Hz), 4.33(1H,brs), 6.69–6.83(3H,m), 7.26–7.32 (5H, m)

MS m/e; 385(M$^+$), 105 (100%)

N-t-butoxycarbonyl-1-methyl-2-[3-methoxy-2-(2-phenylethoxy)-phenyl]ethylamine

NMR (CDCl$_3$) δ(ppm); 0.93(3H,d, J=6.5 Hz),1.40(9H,s), 2.35–2.53(2H,m), 3.09(2H,t,J=6.7 Hz), 3.73(1H,m), 3.82 (3H,s), 4.18(2H,t,J=6.7 Hz), 4.48(1H,brs),6.73(1H,dd,J=1.5, 7.9 Hz),6.76(1H,dd,J=1.5,7.9 Hz),6.96(1H,t, J=7.9 Hz), 7.26–7.32 (5H,m)

MS m/e; 385 (M$^+$), 105 (100%)

EXAMPLE 3

Synthesis of N-t-Butoxycarbonyl-1-(2-Propen-1-yl)-2-[4-Methoxy-3-(2-Phenylethoxy) phenyl]ethylamine (1) 4-Methoxy-3-(2-phenylethoxy)benzaldehyde (51.26 g), dimethyl malonate (26.43 g), piperazine (1.70 g) and acetic acid (1.20 g) were refluxed by heating in 300 ml of benzene under azeotropic dehydration conditions for 8 hours. After the reaction solution was cooled to room temperature, it was washed with water, 1 N hydrochloric acid, a saturated aqueous solution of sodium hydrogencarbonate and a saturated aqueous solution of NaCl in consecutive order and dried over anhydrous magnesium sulfate. The drying agent was separated by filtration and the filtrate was concentrated under reduced pressure. The residue was recrystallized from isopropyl ether-dichloromethane to obtain 67.15 g of methyl 3-[4-methoxy-3-(2-phenylethoxy)phenyl]-2-methoxycarbonylacrylate.

m.p. 104.7–105.9° C.

(2) The methyl 3-[4-methoxy-3-(2-phenylethoxy)phenyl]-2-methoxycarbonylacrylate (66.50 g) was dissolved in 330 ml of ethyl acetate at 40° C. To the solution, 3.33 g of 5% Pd/C was added to hydrogenate at 40° C. until hydrogen absorption was stopped. 5% Pd/C was separated by filtration through a powder magnesium sulfate plate under reduced pressure. The filtrate was concentrated under reduced pressure to obtain 66.51 g of crude methyl 3-[4-methoxy-3-(2-phenylethoxy)phenyl]-2-methoxycarbonylpropionate. This crude compound was used in the subsequent step without purification.

(3) To a solution of the crude methyl 3-[4-methoxy-3-(2-phenylethoxy)phenyl]-2-methoxycarbonylpropionate (7.45 g) in 75 ml of 1,2-dimethoxyethane, 0.80 g of 60% sodium hydride (oily) was added little by little at room temperature under stirring. The resultant solution was stirred further at 40° C. for 1.5 hours. To this solution, 2.66 g of 3-bromo-1-propene was added and stirred at room temperature for 1.5 days. The reaction solution was concentrated under reduced pressure and the residue was dissolved in ethyl acetate. This solution was washed with water, a saturated aqueous solution of sodium hydrogencarbonate and a saturated aqueous solution of NaCl in consecutive order and dried over anhydrous magnesium sulfate. The drying agent was separated by filtration and the filtrate was concentrated under reduced pressure. The residue was purified by silica gel column chromatography (hexane/ethyl acetate=4:1) to obtain 7.76 g of methyl 3-[4-methoxy-3-(2-phenylethoxy) phenyl]-2-methoxycarbonyl-2-(2-propen-1-yl)propionate.

NMR (CDCl$_3$) δ(ppm);2.56(2H,brd,J=7.3 Hz),3.13(2H,t, J=7.66 Hz), 3.16(2H,s), 3.68(6H,s),3.83(3H,s), 4.17(2H,t,J= 7.6 Hz), 5.07–5.16 (2H,m), 5.64–5.84(1H,m), 6.61–6.80 (3H,m),7.17–7.35(5H,m)

MS m/e; 412 (M$^+$), 105 (100%)

(4) To a solution of the methyl 3-[4-methoxy-3-(2-phenylethoxy) phenyl]-2-methoxycarbonyl-2-(2-propen-1-yl)propionate (7.50 g) in 75 ml of methanol, 0.73 g of sodium hydroxide in 1.1 ml of water was added and refluxed by heating for 30 hours under stirring. The reaction solution was concentrated under reduced pressure, and the residue was dissolved in 61 ml of aqueous solution of 3 N sodium hydroxide. The solution was refluxed by heating for 11 hours under stirring. The reaction solution cooled to room temperature was washed with diethyl ether. Then, concentrated hydrochloric acid was added thereto to make the solution acidic. The resultant solution was extracted with dichloromethane and dried over anhydrous magnesium sulfate. The drying agent was separated by filtration and the filtrate was concentrated under reduced pressure. The residue was stirred at 140–150° C. for 4 hours under heating to obtain 6.21 g of crude 3-[4-methoxy-3-(2-phenylethoxy) phenyl]-2-(2-propen-1-yl) propionic acid. This crude compound was used in the subsequent step without purification.

(5) The crude 3-[4-methoxy-3-(2-phenylethoxy)phenyl]-2-(2-propen-1-yl) propionic acid (6.08 g) was treated in the same manner as described in (4) in Example 1 and recrystallized from hexane to obtain 5.46 g of N-t-butoxycarbonyl-1-(2-propen-1-yl)-2-[4-methoxy-3-(2-phenylethoxy)phenyl]ethylamine.

m.p. 94.5–95.3° C.

The following compound was obtained in the same manner as described in (3) of this Example.

Methyl 3-[4-methoxy-3-(2-phenylethoxy)phenyl]-2-methoxycarbonyl-2-(3-methyl-2-buten-1-yl)propionate.

NMR (CDCl$_3$) δ(PPM);1.55(3H,s),1.70 (3H,d,J=1.1 Hz), 2.51(3H,brd,J=7.1 Hz),3.13(2H,t, J=7.6 Hz), 3.15(2H,s), 3.67(6H,s),3.83(3H,s), 4.15 (2H,t,J=7.6 Hz), 5.03–5.10 (1H, m), 6.58–6.79 (3H,m), 7.22–7.33 (5H,m)

MS m/e; 440 (M$^+$), 105 (100%)

Subsequently, the following compound was obtained in the same manner as described in (4) and (5) of this Example.

N-t-butoxycarbonyl-1-(3-methyl-2-buten-1-yl)-2-[4-methoxy-3-(2-phenylethoxy)phenyl]ethylamine m.p. 83.8–84.7° C.

EXAMPLE 4

Synthesis of (−)-N-Propyl-1-(3-Methylbutyl)-2-[4-Methoxy-3-(2-Phenylethoxy)phenyl]ethylamine Hydrochloride (1) To a solution of N-t-butoxycarbonyl-1-(3-methylbutyl)-2-[4-methoxy-3-(2-phenylethoxy)phenyl]ethylamine (89.69 g) in 156 ml of dichloromethane, 156 ml of trifluoroacetic acid was added and stirred at room temperature for 2 hours. The reaction solution was concentrated under reduced pressure, and the residue was dissolved in dichloromethane and washed with a saturated aqueous solution of sodium hydrogencarbonate. The dichloromethane solution was dried over anhydrous sodium sulfate, concentrated under reduced pressure and purified by silica gel column chromatography (chloroform/methanol =30:1–20:1), to thereby obtain 59.65 g of 1-(3-methylbutyl)-2-[4-methoxy-3-(2-phenylethoxy)phenyl]ethylamine.

The thus obtained compound was dissolved in 257 ml of isopropanol, to which 26.58 g of S-(+)-mandelic acid was added and left at room temperature overnight after dissolution on heating. The crystals deposited were recovered by filtration and recrystallized another 4 times from isopropanol. As a result, 30.27 g of an optically active S-(+)-mandelate of 1-(3-methylbutyl)-2-[4-methoxy-3-(2-phenylethoxy) phenyl]ethylamine was obtained.

(2) The optically active S-(+)-mandelate of 1-(3-methylbutyl)-2-[4-methoxy-3-(2-phenylethoxy)phenyl]ethylamine (28.24 g) was separated into layers with diethyl ether and an aqueous solution of 1 N sodium hydroxide. The organic layer recovered was washed with an aqueous solution of 1 N sodium hydroxide and a saturated aqueous solution of NaCl, dried over anhydrous sodium sulfate and concentrated under reduced pressure. To the residue, 100 ml of N,N-dimethylformamide, 7.74 g of propyl bromide and 9.49 g of anhydrous potassium carbonate were added and stirred at room temperature for 6 days. Thereafter, the reaction mixture was concentrated under reduced pressure. Water was added to the residue, which was then extracted with ethyl acetate, washed with water and a saturated aqueous solution of NaCl, dried over anhydrous sodium sulfate and concentrated under reduced pressure. Then, the residue was applied to silica gel column chromatography (chloroform/ethanol=250:1–10:1), and the resultant compound was converted into a hydrochloride with a solution of 4 N hydrogen chloride/dioxane. Thereafter, recrystallization from toluene-hexane yielded 16.20 g of (−)-N-propyl-1-(3-methylbutyl)-2-[4-methoxy-3-(2-phenylethoxy)phenyl]ethylamine hydrochloride.

m.p. 99.0–100.0° C.

$[\alpha]_D^{30.0}$=−21.72 (c=0.580; CHCl$_3$)

The following compound was obtained in the same manner.

(−)-N-propyl-1-butyl-2-[4-methoxy-3-(2-phenylethoxy)-phenyl]ethylamine hydrochloride m.p. 83.0–84.0° C.

$[\alpha]_D^{30.0}$=−21.10 (c=0.408; CHCl$_3$)

Further, the following (+) isomers were obtained in the same manner except that R-(−)-mandelic acid was used instead of S-(+)-mandelic acid.

(+)-N-propyl-1-(3-methylbutyl)-2-[4-methoxy-3-(2-phenylethoxy)-phenyl]ethylamine hydrochloride m.p. 98.0–99.0° C.

$[\alpha]_D^{30.0}$=+21.92 (c=0.456; CHCl$_3$)

(+)-N-propyl-1-butyl-2-[4-methoxy-3- (2-phenylethoxy)-phenyl]ethylamine hydrochloride m.p. 82.5–83.5° C.

$[\alpha]D^{30.0}$=+22.20 (c=0.414; CHCl$_3$)

Test Example 1

Receptor Binding Experiment

As experimental animals, Hartley guinea pigs were used. A sigma receptor binding experiment was performed in accordance with the following method described in European Journal of Pharmacology, Vol. 251, p. 121 (1994) using [$^3$H] (+)-pentazocine (sigma 1) or [$^3$H]1,3-di-o-tolylguanidine (DTG) (sigma 2) as a [$^3$H]-labelled ligand.

A membrane specimen prepared from the total brains of guinea pigs, a [$^3$H] ligand and a test drug were reacted in 50 mM Tris-HCl buffer (pH 7.4). For examining sigma 1, [$^3$H](+)-pentazocine (2 nM) as a [$^3$H] ligand was reacted at 25° C. for 120 minutes. For examining sigma 2, [$^3$H] DTG (1 nM) as a [$^3$H] ligand was reacted in the presence of 10$^{-7}$ M (+)-pentazocine at 25° C. for 90 minutes. After the completion of the reaction, the reaction solution was vacuum filtered through a glass filter (GF/B), and the radioactivity of the filter was determined with a liquid scintillation spectrometer.

The binding which occurred in the reaction in the presence 10 μM haloperidol was regarded as non-specific binding, and the difference obtained by subtracting non-specific binding from the total binding was regarded as specific binding. An inhibition curve was obtained by reacting a [$^3$H] ligand at a specific concentration with a test drug at varied concentrations under the conditions described above. From this inhibition curve, the concentration of the test drug which inhibits individual binding by 50% (IC$_{50}$) is obtained. The results are shown in Table 1.

TABLE 1

| Test Drug | Sigma 1 (nM) | Sigma 2 (nM) |
|---|---|---|
| A | 0.46 | 204.5 |
| B | 0.73 | 233.0 |

A: (−)-N-propyl-1-(3-methylbutyl)-2-[4-methoxy-3-(2-phenylethoxy)-phenyl]ethylamine hydrochloride
B: (−)-N-propyl-1-butyl-2-[4-methoxy-3-(2-phenylethoxy)phenyl]ethylamine hydrochloride Industrial Applicability The compound of the invention is excellent in sigma 1 receptor antagonism and useful for treating schizophrenia, depression, anxiety, cerebrovascular diseases/senile troublesome behaviors, and cognitive dysfunctions and motor dysfunctions such as Alzheimer's disease, Parkinson's disease and Huntington's disease which are neurodegenerative diseases. Further, the compound of the invention is also useful for treating dependence resulted from drug abuse (narcotics, antihypnotics, alcohols, psychotropics, marihauna, etc.).

It is claimed:

1. An optically active compound, which is a substituted phenylalkylamine derivative and is represented by the following formula:

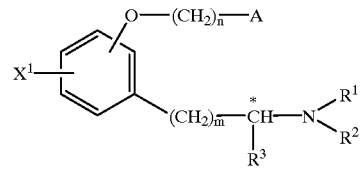

wherein A is a substituted or non-substituted phenyl or thienyl; X$^1$ is hydrogen, halogen, hydroxyl or a substituted or non-substituted C$_{1-5}$ alkoxy; R$^1$ and R$^2$ are the same or difference and are hydrogen, C$_{1-7}$ alkyl, C$_{3-7}$ alkenyl or C$_{3-7}$ alkynyl; R$^3$ is C$_4$ or C$_5$ alkyl; n is an integer from 2 to 5; and m is an integer from 1 to 4, or a pharmaceutically acceptable salt thereof.

2. The compound of claim 1, wherein R$^3$ is butyl.

3. The compound of claim 1, wherein R$^3$ is 3-methylbutyl.

4. The compound of claim 1, wherein $R^1$ is hydrogen; $R^2$ is propyl; $R^3$ is 3-methylbutyl or butyl; $X^1$ is 4-methoxy; and A—$(CH_2)$n-O is 3-(2-phenylethoxy).

5. An antipsychotic composition comprising the compound of claim 1 and an excipient or binder.

6. A method for blocking sigma 1 receptor in a patient in need thereof, comprising administering to the patient an amount of the compound of claim 1 effective to block sigma 1 receptor in the patient.

* * * * *